United States Patent
Wyatt et al.

(10) Patent No.: US 10,408,716 B2
(45) Date of Patent: Sep. 10, 2019

(54) METHOD AND APPARATUS TO MEASURE MULTIPLE SIGNALS FROM A LIQUID SAMPLE

(71) Applicant: Wyatt Technology Corporation, Goleta, CA (US)

(72) Inventors: Philip J. Wyatt, Santa Barbara, CA (US); Vincent H. Hsieh, Santa Barbara, CA (US); Mario Yasa, Santa Barbara, CA (US); Barbara R. Maurer, San Jose, CA (US); David Cannell, Santa Barbara, CA (US); Steven P. Trainoff, Santa Barbara, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

(21) Appl. No.: 15/761,808

(22) PCT Filed: Sep. 21, 2016

(86) PCT No.: PCT/US2016/052955
§ 371 (c)(1),
(2) Date: Mar. 20, 2018

(87) PCT Pub. No.: WO2017/053478
PCT Pub. Date: Mar. 30, 2017

(65) Prior Publication Data
US 2018/0259430 A1 Sep. 13, 2018

Related U.S. Application Data

(60) Provisional application No. 62/221,879, filed on Sep. 22, 2015.

(51) Int. Cl.
*G01N 21/05* (2006.01)
*G01N 1/28* (2006.01)
(Continued)

(52) U.S. Cl.
CPC .......... *G01N 1/286* (2013.01); *B01F 5/0647* (2013.01); *G01N 21/05* (2013.01); *G01N 21/51* (2013.01);
(Continued)

(58) Field of Classification Search
CPC .. G01N 1/286; G01N 2001/2866; G01N 1/38; G01N 2021/052; G01N 2021/513;
(Continued)

(56) References Cited

U.S. PATENT DOCUMENTS 4,019,372 A * 4/1977 Parkell ................... G01N 21/05
 210/198.2
4,051,025 A * 9/1977 Ito .......................... G01N 30/42
 210/198.2
(Continued)

FOREIGN PATENT DOCUMENTS

GB 2517997 A 3/2015
JP S58201050 A 11/1983
(Continued)

OTHER PUBLICATIONS

International Search Report for PCT/US16/52955, Dec. 8, 2016
(Continued)

*Primary Examiner* — Michael P Stafira
(74) *Attorney, Agent, or Firm* — Leonard T. Guzman

(57) ABSTRACT

One or more homogenizing elements are employed in a flow through, multi-detector optical measurement system. The homogenizing elements correct for problems common to multi-detector flow-through systems such as peak tailing and non-uniform sample profile within the measurement cell. The homogenizing elements include coiled inlet tubing, a flow distributor near the inlet of the cell, and a flow distributor at the outlet of the cell. This homogenization of the sample mimics plug flow within the measurement cell
(Continued)

and enables each detector to view the same sample composition in each individual corresponding viewed sample volume. This system is particularly beneficial when performing multiangle light scattering (MALS) measurements of narrow chromatographic peaks such as those produced by ultra-high pressure liquid chromatography (UHPLC).

12 Claims, 18 Drawing Sheets

(51) Int. Cl.
  *B01F 5/06* (2006.01)
  *G01N 30/74* (2006.01)
  *G01N 21/51* (2006.01)
(52) U.S. Cl.
  CPC ..... *G01N 30/74* (2013.01); *G01N 2001/2866* (2013.01); *G01N 2021/052* (2013.01); *G01N 2021/513* (2013.01)
(58) Field of Classification Search
  CPC .. G01N 2035/041; G01N 21/05; G01N 21/51; G01N 30/74; G01N 35/00732; G01N 35/0099; G01N 35/02; G01N 35/10; G01N 35/1081
  See application file for complete search history.

(56) References Cited

U.S. PATENT DOCUMENTS

| | | | |
|---|---|---|---|
| 4,228,007 A * | 10/1980 | Rausch | B01D 15/206 210/198.3 |
| 4,582,608 A * | 4/1986 | Ritacco | B01D 15/22 210/198.2 |
| 4,907,884 A | 3/1990 | Wyatt et al. | |
| 5,032,283 A * | 7/1991 | Scott | G01N 30/38 210/198.2 |
| 5,167,810 A | 12/1992 | Vassarotti et al. | |
| 5,305,071 A | 4/1994 | Wyatt | |
| 5,530,540 A | 6/1996 | Wyatt et al. | |
| 5,900,152 A | 5/1999 | Janik et al. | |
| 6,171,486 B1 * | 1/2001 | Green | B01D 15/22 210/198.2 |
| 2008/0135484 A1 * | 6/2008 | Hammer | G01N 30/92 210/656 |
| 2009/0255601 A1 * | 10/2009 | Baeuerle | B01F 5/061 137/892 |

FOREIGN PATENT DOCUMENTS

| | | |
|---|---|---|
| JP | S61120947 A | 6/1986 |
| JP | H08122328 A | 5/1996 |
| JP | H09127086 A | 5/1997 |
| JP | 2000230887 A | 8/2000 |
| JP | 2008530985 A | 8/2008 |
| WO | 2006083907 A2 | 8/2006 |

OTHER PUBLICATIONS

Written Opinion for PCT/US16/52955, Dec. 8, 2016.
Supplementary European Search Report for European Patent Application EP 16 84 9540.

* cited by examiner

METHOD AND APPARATUS TO MEASURE MULTIPLE SIGNALS FROM A LIQUID SAMPLE

PRIORITY

This application claims priority to U.S. Provisional application No. 62/221,879, filed Sep. 22, 2015, and to PCT Application No. PCT/US2016/052955, filed Sep. 21, 2016.

RELATED PATENTS

The following references related to the background and application of the present invention are hereby incorporated by reference:
Steven P. Trainoff, U.S. Pat. No. 7,386,427 B2, issued 10 Jun. 2008, "Method for correcting the effects of interdetector band broadening";
Steven P. Trainoff, U.S. Pat. No. 7,911,594 B2, issued 22 Mar. 2011, "Method to derive physical properties of a sample after correcting the effects of interdetector band broadening";
Gary R. Janik, et al., U.S. Pat. No. 5,900,152, issued 4 May 1999, "Apparatus to reduce inhomogeneities in optical flow cells";
Gary R. Janik, et al., U.S. Pat. No. 5,676,830, issued 14 Oct. 1997, "Method and apparatus for reducing band broadening in chromatographic detectors";
Steven D. Phillips, et al., U.S. Pat. No. 4,616,927, issued 14 Oct. 1986, "Sample cell for light scattering measurements";
Raymond P. W. Scott and Elena Katz, U.S. Pat. No. 5,032,183, issued 16 Jul. 1991, "Low dispersion fluid conduit useful in chromatography systems"; and
Steven P. Trainoff, U.S. Pat. No. 7,982,875, issued 19 Jul. 2011, "Improved method and apparatus for measuring the scattered light signals from a liquid sample."

DEFINITIONS

By "particle," we refer to such objects as protein and polymer molecules together with their conjugates and co-polymers, viruses, bacteria, virus-like particles, liposomes, polystyrene latex particles, nanoparticles, and all such particles within the approximate size range of one to a few thousand nanometers.

The terms quasi-elastic light scattering (QELS), dynamic light scattering (DLS), and photon correlation spectroscopy (PCS) are frequently used to describe the same phenomenon, namely the measurement of scattered light from particles undergoing Brownian motion. In this specification we will use the term QELS, but it should be noted that QELS is equivalent to the other mentioned terms often used in the art. QELS stands distinct from other light scattering measurement techniques, the most common of which is multi-angle light scattering (MALS), formerly referred to as "Differential Light Scattering," which measures the angular dependence of light scattered from a solution of particles.

Throughout this specification reference will be made to optical measurement cells. There are, in the most general form, two cell types that will be discussed herein. The first is a cell, such as that disclosed in U.S. Pat. No. 4,616,927, wherein the direction of flow of the liquid sample and solvent through the cell runs along the same path essentially parallel to the illuminating beam. This cell configuration will be referred to as a "parallel cell." An alternative cell design discussed herein is one wherein the fluid flow runs transverse to the illuminating beam. This cell configuration will be referred to as a "perpendicular cell." This is the traditional structure used for measurement of light scattered from a cylindrical container. It should be noted that this nomenclature should not be indicative of a strict limitation, but rather provide a general description and designation only. For example, the beam traversing a parallel cell may be slanted at a small angle, such that at the entrance of the cell the beam almost grazes the bottom of the bore, while at the exit it almost grazes the top of the bore, and still be considered a "parallel cell" even though the flow and the beam are not precisely parallel. Indeed, in several embodiments of the invention, it may be desirable to direct the beam through the sample at an angle in order to minimize reflections, reduce noise, etc. The optical measurement cells discussed above and throughout the specification are flow through cells which contain a bore through which the liquid sample passes. While these bores are generally of a circular or near circular cross section, the sample bore should not be considered limited to this shape. The present invention is applicable to cells with bores cross sections in a variety of shapes, including rectangular, half-circular, elliptical, triangular, etc., as well as irregular shape in cross section and path.

There are many means by which particles of various sizes, masses and charges in a liquid sample may be separated from their constituents. In this disclosure we will focus primarily on a technique generally referred to as ultra-high pressure liquid chromatography (UHPLC), which is also known as ultra-high performance liquid chromatography, however it should be noted that most separation techniques used today are species under the genus liquid chromatography, and all liquid chromatography techniques can benefit from the invention disclosed herein. Therefore, while the discussion below will primarily refer to UHLPC (sometimes also referred to by the trade name UPLC®), as it is the method which benefits most from the present invention, the invention is also applicable to other liquid chromatography techniques such as high pressure liquid chromatography (HPLC), which is frequently referred to as size exclusion chromatography (SEC) or gel permeation chromatography (GPC), and reversed phase chromatography. In addition the invention is also applicable to use with other flow based separation techniques, such as field flow fractionation (FFF), wherein the separated sample is delivered to the detection cell via a tube.

BACKGROUND

The analysis of macromolecular or particle species in solution is usually achieved by preparing a sample in an appropriate solvent and then injecting an aliquot thereof into a separation system such as a liquid chromatography (LC) column or Field Flow Fractionation (FFF) channel wherein the different species of particles contained within the sample are separated into their various constituencies. Once separated by such means, generally based on size, mass, or column affinity, the samples are subjected to analysis by means of light scattering, refractive index, UV absorption, electrophoretic mobility, viscometric response, etc. In this disclosure we will primarily concern ourselves with multi-angle light scattering (MALS).

A typical HPLC-MALS setup is shown in FIG. 2. Solvent is generally drawn by an HPLC pump 201 from a solvent reservoir 202 through a degasser 203 and then pumped through filtering means 204 to the injection valve 211. A liquid sample 205 is injected into the sample loop 212 of the injection valve 211, generally by a syringe 206. The sample, however, may be added to the flow stream by means of an auto injector rather than the manual means described. The fluid sample then flows from the injector through one or more HPLC columns 207, where the molecules or particles contained within the sample are separated by size, with the largest particles eluting first. The separated sample then passes sequentially through a MALS detector 208 and a concentration detector such as a differential refractometer 209 before passing to waste. Other instruments capable of measuring the physical properties of the molecules or particles in the sample may also be present along the flow stream. For example, a UV/Vis absorbance detector and/or a viscometer might be present within the chain of instruments. In general, data generated by the instruments is transmitted to a computer that is capable of collecting, storing, and analyzing the data and reporting the results to the user.

As discussed above, a sample containing aliquot is injected into a separation system, such as the HPLC system shown in FIG. 2, or, as relates more closely to the present invention, a UHPLC system which is similar but wherein the columns 207 are one or more UHPLC columns rather than HPLC columns, and the pump 201 is capable of producing the higher pressures at which UHPLC systems operate. The columns separate the sample by size into its constituent fractions. Each of these eluting and separated fractions results in a "peak" which passes via tubing to a measurement volume. Each detection instrument measures, in turn, a signal from the peak as it passes through the measurement volume. A single aliquot may generate any number of peaks, for example, a monodisperse sample of single particle size will generate only one peak. As each sample peak passes through a measurement volume a signal will be detected that relates to the sample being analyzed at any given instant as it passes through the cell. These finite measurements are often referred to as "slices," each slice representing the instantaneous measurement of the sample being detected at a given volume of eluent flowing through the cell. These signals are digitized and stored in a computer, and the resultant data is generally reported to the user as a peak 301, such as that shown in FIG. 3, wherein each element of the peak represents a given slice. The data at a given slice, in this case the light scattering data over a plurality of angles, 302, corresponding to a single slice 302a may be viewed and analyzed utilizing a software program such as ASTRA®. The data shown in FIG. 3 also includes the signal 303 recorded from a differential refractometer.

A DETAILED DESCRIPTION OF THE INVENTION

Figure 1:
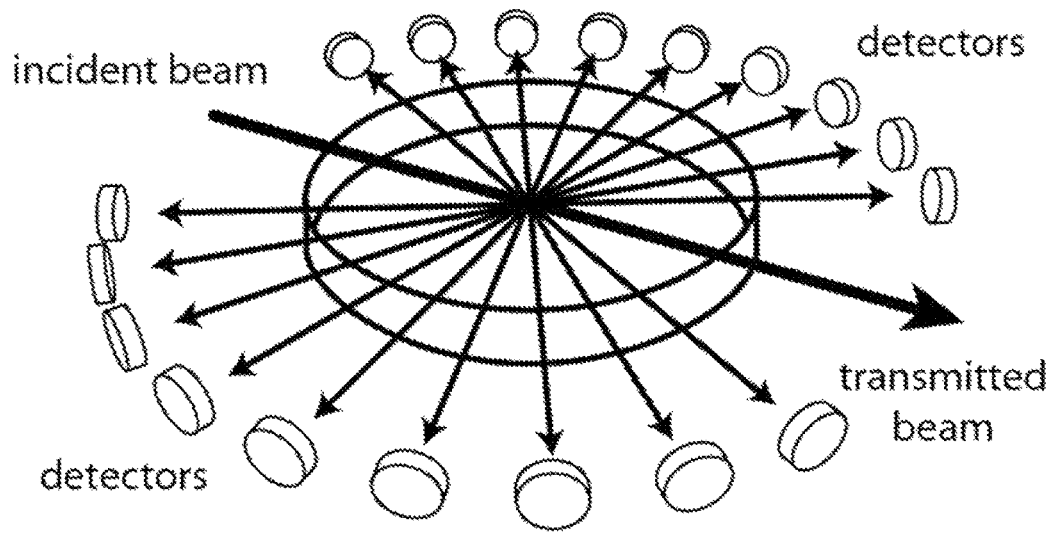
FIG. 1 shows a geometry schematic of a MALS measurement.
Figure 2:
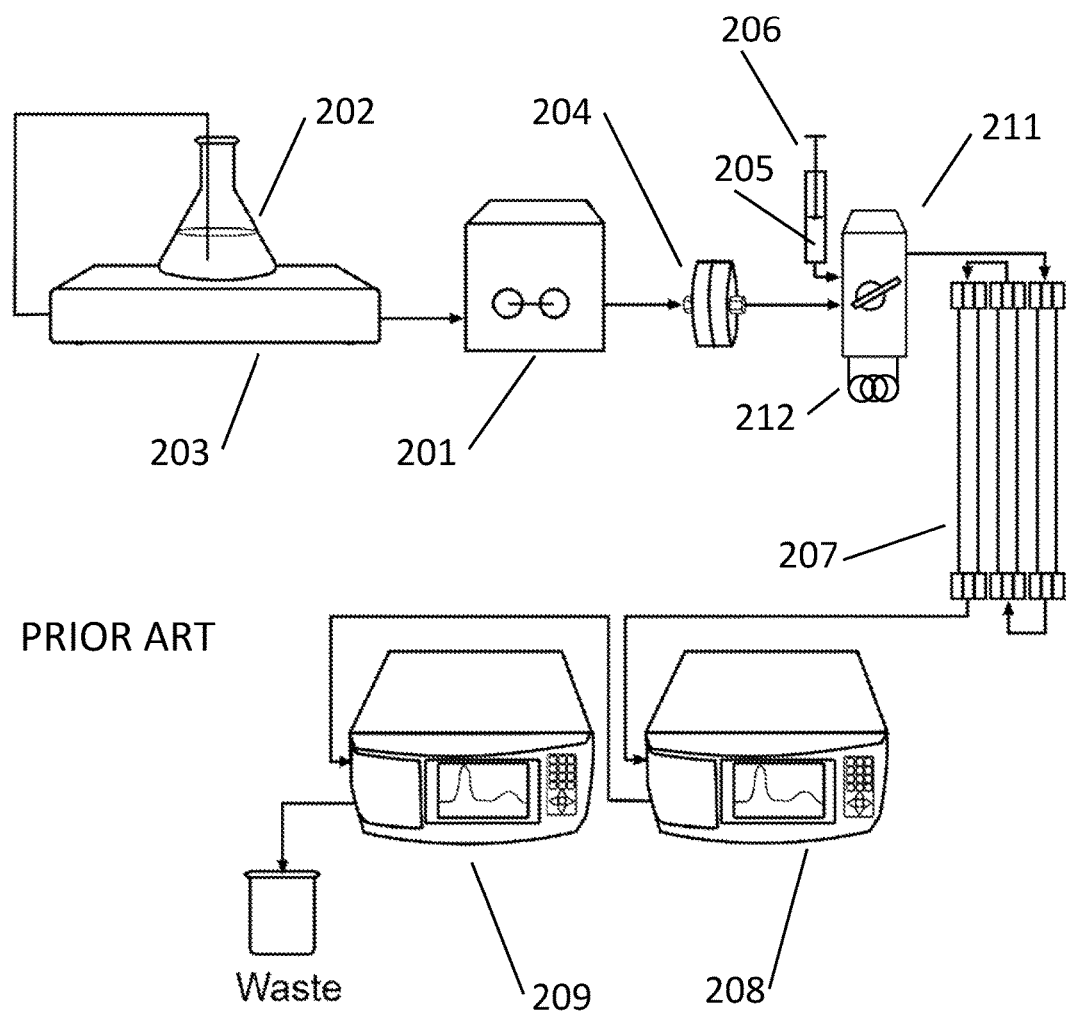
FIG. 2 shows a typical HPLC-MALS configuration of the various elements associated with a MALS measurement.
Figure 3:
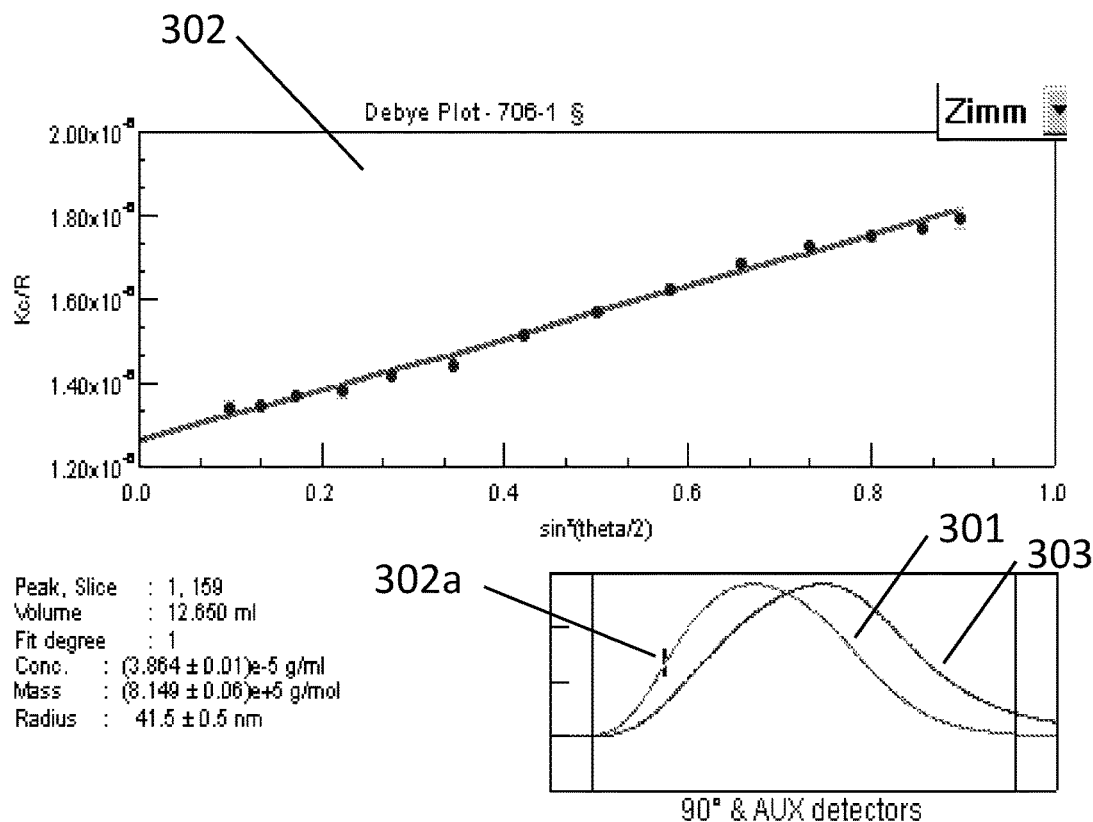
FIG. 3 is an example of MALS and concentration data collected over an entire peak including MALS data displayed for a single slice.
Figure 4:
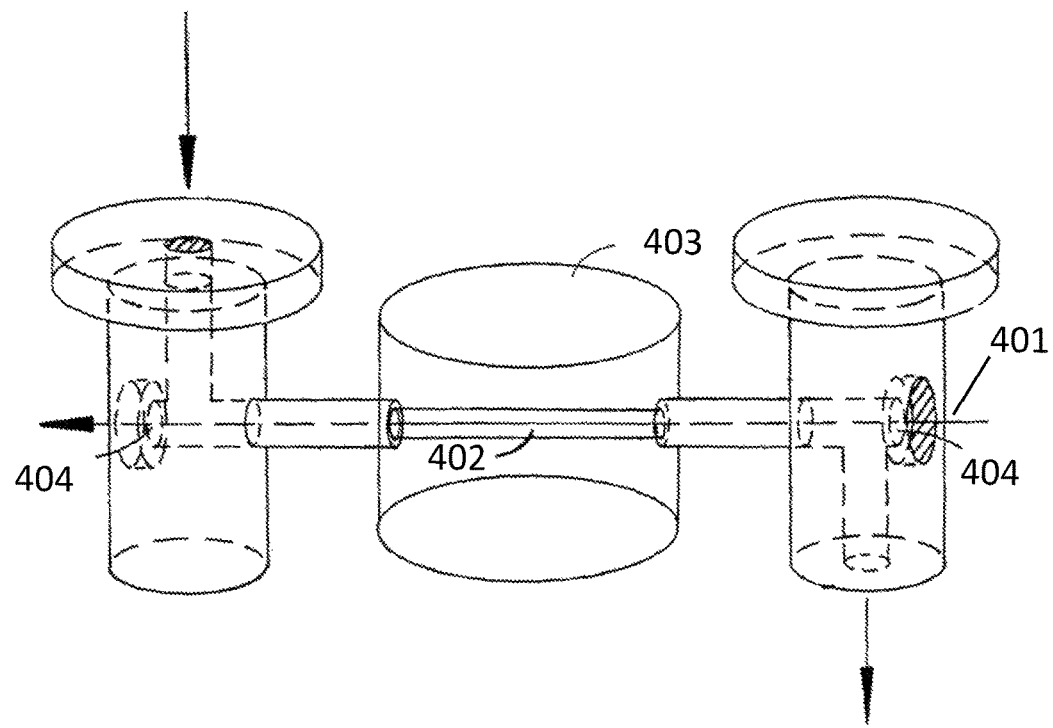
FIG. 4 shows the parallel cell structure for light scattering measurements and associated manifold system of U.S. Pat. No. 4,616,927.

MALS detection systems have frequently employed a flow cell wherein a horizontal bore defines the region of both fluid flow and the path along which the measurement beam traverses the cell. Such a cell was disclosed in U.S. Pat. No. 4,616,927. The cell, herein referred to as a parallel cell, is a section of a cylinder as shown in FIG. 4, with a bore drilled through a diameter. This cell design further acts as a lateral lens, such that the beam 401 acts as a line source near the detection region 402 at which a plurality of detectors (not shown) positioned at various angles around the circumference of the cell are directed to receive light scattered therefrom by the sample. Therefore, while this innovative design allowed for the gathering of more light from the detector at a given scattering angle, this benefit comes at the cost of some averaging of the sample concentration naturally occurring along the breadth of the line source along the flow path at a given measured angle due to the larger sample volume required for this design. Another means by which the amount of light scattered at a given angle is increased was disclosed in U.S. Pat. No. 7,982,875, is a modification to the cell disclosed in U.S. Pat. No. 4,616,927, where the sample cell acts as both a vertical and lateral lens.

Figure 5:
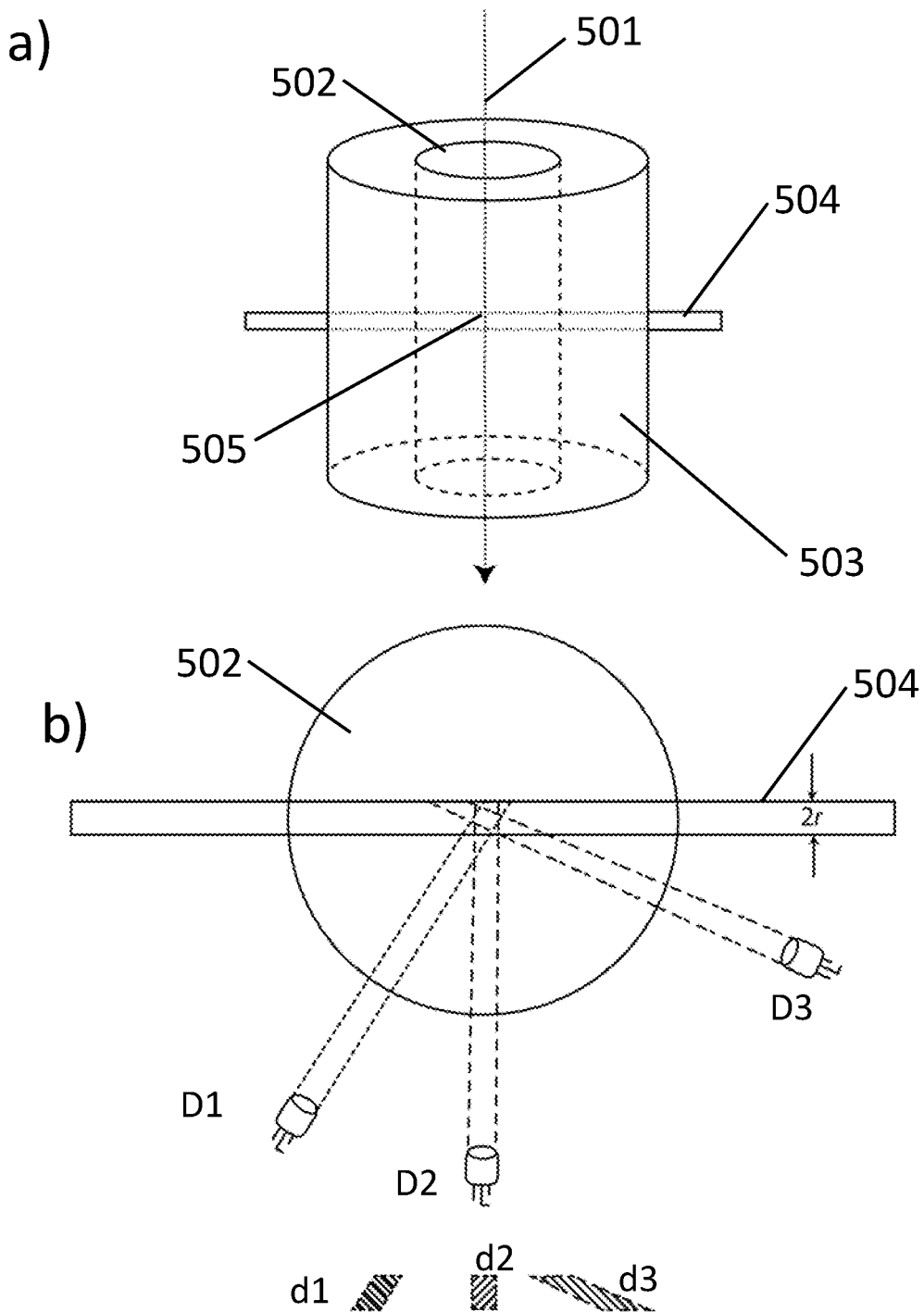
FIG. 5 illustrates an alternative light scattering cell configuration that contrasts in its flow path with that of the cell of FIG. 4.

The trend in the industry to lower sample volumes that produce correspondingly lower volume peaks has driven the advent of Ultra High Pressure Liquid Chromatography (UHPLC). As a result MALS detection systems for measuring UHPLC peaks must appropriately scale in sensitivity and volume. Liquid samples passing through the measurement cell, either the parallel cell as discussed above, or an alternative configuration, such as that shown in FIG. 5(a), and referred to as a perpendicular cell, are greatly affected by the flow mechanics of the sample as it enters the cell. In the perpendicular cell, the sample flow 501 enters the bore 502 of the cell structure 503 perpendicularly to the beam 504. An array of detectors situated about the measurement cell collect scattered light. Ideally each detector would view the same illuminated volume, however, due to non-perfect alignment and variation in the geometry of the sample volume seen detector located at different angles, they necessarily view slightly different volumes and therefore it is essential that the sample be uniformly distributed throughout the cell. An example of the variability in the geometry of the scattered volume based on the field of view of detectors placed at different angles is shown in FIG. 5(b). A laser beam 504 of diameter 2r passes through the bore 502 of the measurement cell. Three detectors D1, D2 and D3 are placed about the cell and each is directed to detect scattering from the illuminated sample near the center of the cell. However, each of the three detectors has a unique field of view which results in detection regions whose corresponding observed scattering volumes d1, d2, and d3 vary. In this example detector D3, located at 90° to the laser beam will have the smallest scattering volume, while detector D3, located at a low angle, will have the largest. If the sample concentration is uniform across all of the measured scattering volumes d1, d2, and d3, the signals may simply be normalized to unity. However, if the sample profile as it passes through the beam is non-uniform, not only will each sample view a different sized scattering volume, but the variation in the geometry of the scattering volumes will cause each detector to view different sample passing there through. It is therefore critically important that the sample be homogeneous throughout the range measured scattering volumes seen by individual detectors.

Figure 6:
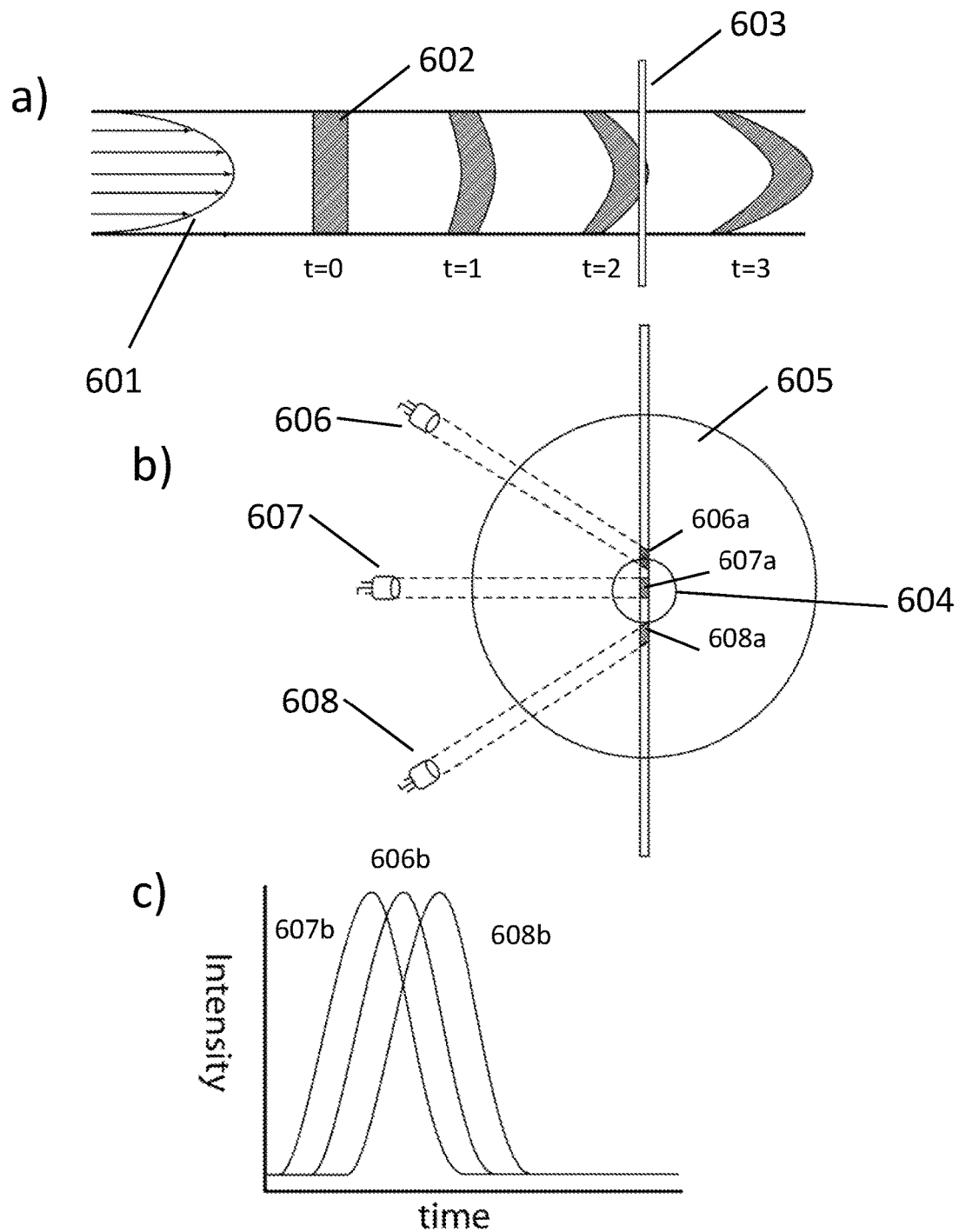
FIG. 6 illustrates (a) a flowing sample subject to spreading due to Poiseuille flow, (b) the field of view of three misaligned detectors collecting scattered light from a sample cell, and (c) the intensity vs. time plots illustrating the time shift seen by each detector due to misalignment.

Issues of sample uniformity are particularly evident with UHPLC as the peak widths are comparable to the sample volume of the measurement cell. Laminar flow along the capillary tubing results in Poiseuille flow during transit of the separated sample from the UHPLC system to the measurement cell. In Poiseuille flow the velocity profile is parabolic where the fluid flow at the wall of the tubing is zero, and the flow in the center of the tube is at a maximum which is theoretically 1.5 times that of the average flow of a sample region. As shown in FIG. 6, the Poiseuille flow profile 601 causes a narrow sample peak 602 exiting the separation system to be broadened over time as it passes through a bore, be it a length of tubing or a measurement cell. Under these conditions any mild misalignment of the detectors wherein each detector views a slightly different illuminated volume can cause each detector to measure a slightly different section of the sample passing through the cell at a given instant in time. For example, consider the sample profiles shown in FIG. 6a wherein the sample is traveling down a detection cell and beam 603 traverses the cell at the point indicated as the sample, at time t=2, passes through. A cross section of the sample at the beam interface is shown in FIG. 6b. At time t=2, the front of the sample has reached a region indicated as section 604, whereas section 605 consists of only solvent. Three different light scattering detectors are oriented towards the center of the cell, but slight variations in alignment cause them to see different regions of the illuminated beam. Therefore the first detector 606 detects light scattered from a region 606a, wherein part of the beam within the detection area illuminates the sample 604. The second detector 607 sees a different region 607a wherein light is scattered exclusively from the sample 604, and the third detector 608, at time t=2 sees no sample scattering at all. This effect causes a time shift in the intensity peaks recorded for each a detector; the intensity vs. time plot for each detector is represented in FIG. 6c. It should be noted that if perfect alignment were achieved, that is, if each detector viewed the exact same measurement volume, this time variation with respect to intensity recorded at each detector would not be present in the same manner, but measurements could still suffer from some temporal misalignment of the peaks due to the different scattering volumes defined by the intersection of the beam and the solid scattering angle viewed by each detector discussed above.

Figure 7:
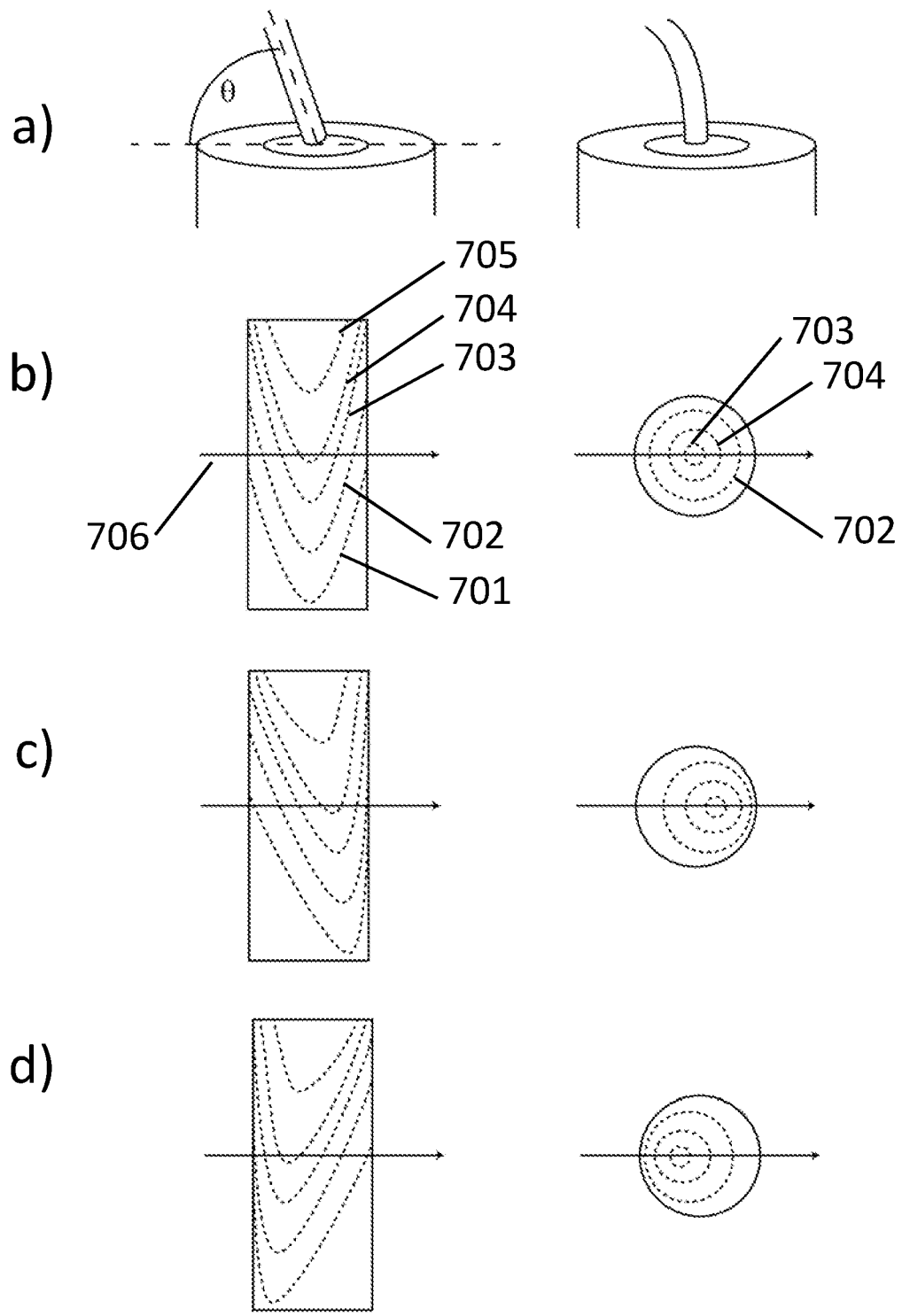
FIG. 7 shows examples flow profiles within a measurement cell due to Dean flow from bent or improperly directed inlet tubing.

Dispersion, as the sample enters the measurement cell, exacerbated by the phenomena of Dean Flow and convective diffusion, wherein radial non-uniformity from slight bends in the inlet tubing cause the sample to enter the cell asymmetrically introducing error into the measurement due to a time delay in the light scattering signal reaching the individual detectors. It has been shown in literature, for example see A. Kaufman, et. al., "Extra-Column Band Spreading Concerns in Post-Column Photolysis Reactors for Microbore Liquid Chromatography," Current Separations, 17(1) 9-16 (1998), that peak dispersion in bent or coiled tubes can be described by the dimensionless parameter $Dn^2Sc$ where Dn is the Dean number $$Dn = Re\sqrt{\frac{r_t}{r_c}} \quad (3)$$

where $r_t$ and $r_c$ are the tube inner diameter and the tube bend radius respectively and Re the Reynolds number and Sc is the Schmidt number $$Sc = \frac{\eta}{D_m \rho} \quad (4)$$

where $D_m$ is the sample diffusion coefficient, $\eta$ the solvent viscosity and $\rho$ the solvent density. It has been found that a $Dn^2Sc$ of less than 100 has little impact on peak dispersion while greater values can have a significant influence. FIG. 7 shows a sample with a Poiseuille profile entering in a measurement cell consisting of various bands of sample concentration. Each contour line 701, 702, 703, 704, 705 represents a boundary of a given sample concentration band. If the sample enters the cell through a tube that is perfectly parallel to the bore and with no contribution from Dean Flow, $r_c=\infty$, the sample boundaries will be concentric at the plane defined by the bore of the sample cell where it is intersected by the illuminating beam 706 as shown in FIG. 7(b). However, any asymmetry caused, for example, by an improperly angled or connected inlet tubing, or by radial non-uniformity as a result of Dean Flow from a curved tube, as indicated in FIG. 7(a) will cause a profile such as those shown in FIGS. 7(c) and 7(d). As discussed above, if we consider a MALS detection system with three separate detectors oriented so as to detect light scattered from the illuminating beam by the sample as it passes there through, we can see how, if each detector is perfectly aligned to the same region of the cell, each will "see" the same band of the sample, to the extent to which the variation in detection geometry of each detector discussed above allows, even when the sample is asymmetrically distributed. However, perfect alignment, although desired is never practically achieved, and therefore, as was previously shown in FIG. 6, each detector will be measuring a different region of concentration as the sample passes through the illuminating beam. Therefore there will always be small variations in sample volume that are within the field of view of each of the three detectors at a given instant in time. This issue is further exacerbated with the addition of more detectors.

Figure 8:
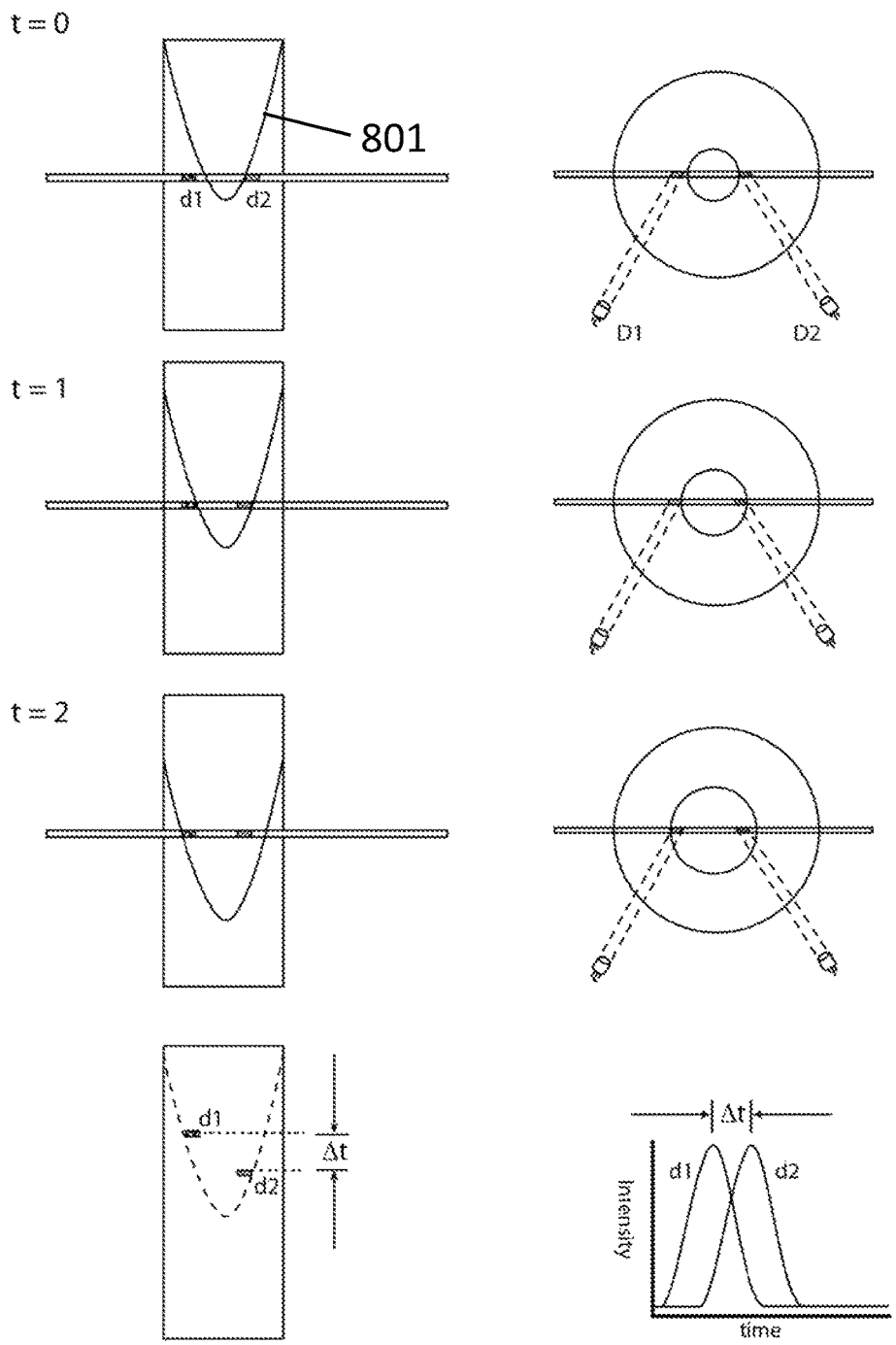
FIG. 8 shows the difference in time for a single concentration profile front to pass two detectors that view slightly different detection volumes.

The time shift between detectors is further explained by way of FIG. 8 wherein a single concentration contour is shown and there are two detection volumes defined by the field of view of two separate detectors. In this case the detection volumes are labeled $d_1$, and $d_2$. The contour line 801 represents the boundary of a given concentration of sample. The time at which the two detectors see the sample following contour line 801 varies depending on the lateral positioning of the detector field of view. At time t=0, neither detector is seeing an illuminated volume of sample. The contour line 801 moves downward as the sample travels through the capillary between t=0 and t=2. At time t=1, D2 sees the sample following the contour 801, at time t=2, D1 sees the contour, and therefore the time delay, $\Delta t$, is simply $t_2-t_1$. Again the intensity vs. time peak is shown graphically in FIG. 8c.

Another issue complicating the accurate measurement of light scattering from separated peaks involves peak tailing, which is a result of axial broadening along the capillary and is caused directly by laminar flow within the tubing. The flow velocity at the edges of the tubing is zero so any sample near this boundary can take a very long time to elute into the measurement cell.

Therefore, in order to improve the reliability of MALS and other optical measurements after separation, particularly UHPLC separation, all of these issues: peak tailing, non-uniform sample profile entry into the measurement cell, and Poiseuille flow within the tubing and sample cell, may be addressed by the inventive methods and apparatus disclosed herein. This invention seeks to promote plug flow of the sample through the cell whenever possible and improve symmetry of the flow profile within the sample cell. Plug flow is a simple velocity profile of flow through a tube wherein each element across the tube diameter has the same velocity. Therefore, plug flow stands in stark contrast to Poiseuille flow discussed above.

Figure 9:
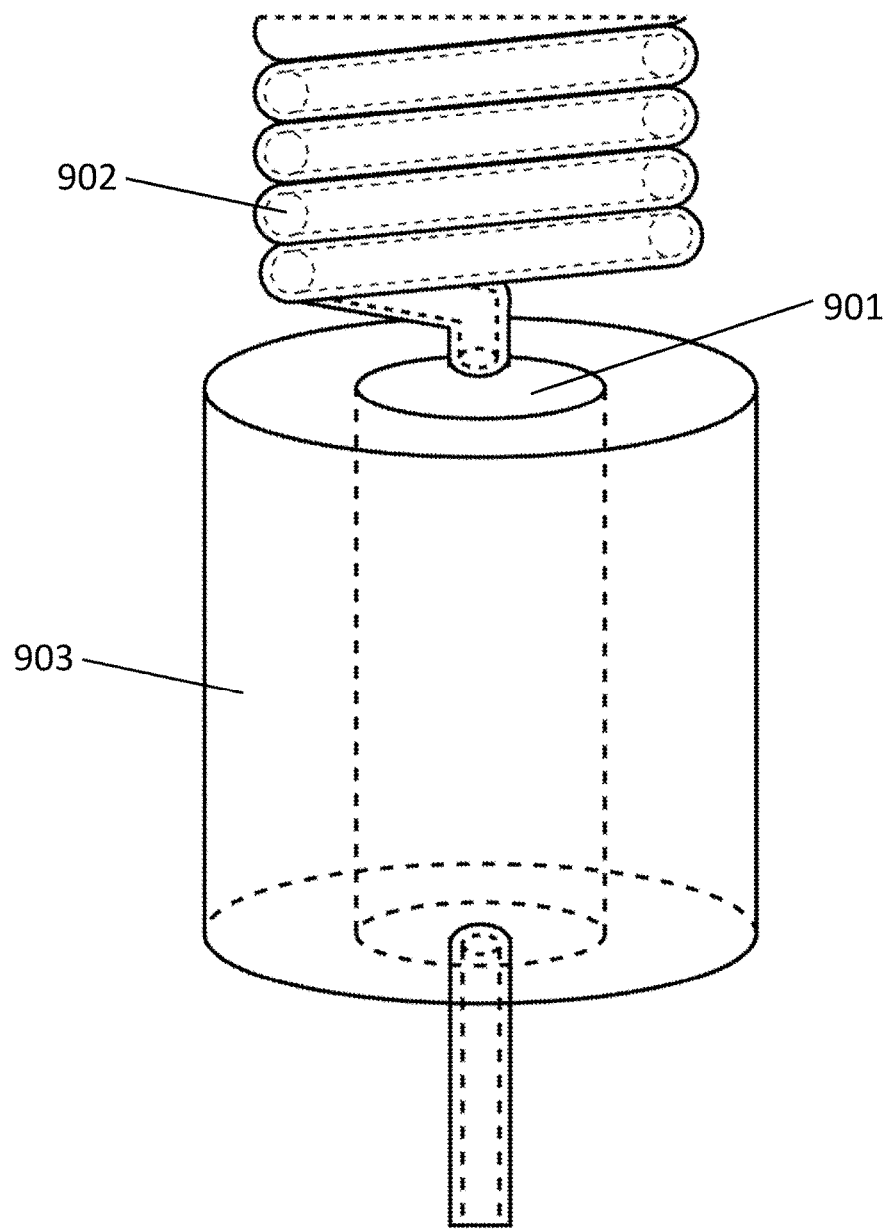
FIG. 9 shows a schematic representation of an embodiment of the inventive measurement system employing a helical, coiled inlet tube that corrects for asymmetrical flow profiles within the inlet tube.

The first issue to be addressed is the non-uniformity of the sample within the tubing as it enters the flow cell. The present invention, one embodiment of which is shown in FIG. 9, makes use of a length of coiled tubing 902 designed, as discussed below, to disrupt Poiseuille flow and contributions due to Dean Flow prior to entry of the sample into the flow cell. The coiled tubing promotes radial mixing transverse to the flow path, creating, by the time the fluid enters the cell, an equal distribution across the breadth of the inlet tubing, resulting in a symmetrical flow profile, with respect to the bore, to enter the flow cell. The coiled tubing also promotes Taylor dispersion causing shear flow to increase the effective diffusion coefficient of the sample away from the tubing wall. This effect helps to mitigate peak tailing as discussed above. The narrow bore tube 902, generally made of stainless steel, is formed in a helix shaped coil wherein the turn radius of the tubing is preferably about 15 times the inner radius of the tubing. Although coiled tubing may be less efficient for this type of mixing than one comprising a serpentine path, it is more easily manufactured and maintained in a useful shape. After passage of the sample through the coiled tubing 902, it passes along the measurement cell through the illuminating beam to the cell outlet, where it passes to the outlet cell which may also be connected to a length of coiled tubing as the sample passes to the next instrument in the chain or to waste. Surrounding the cell are a set of photo detectors which collect light scattered from the sample by the illuminating beam at a plurality of scattering angles.

Figure 10:
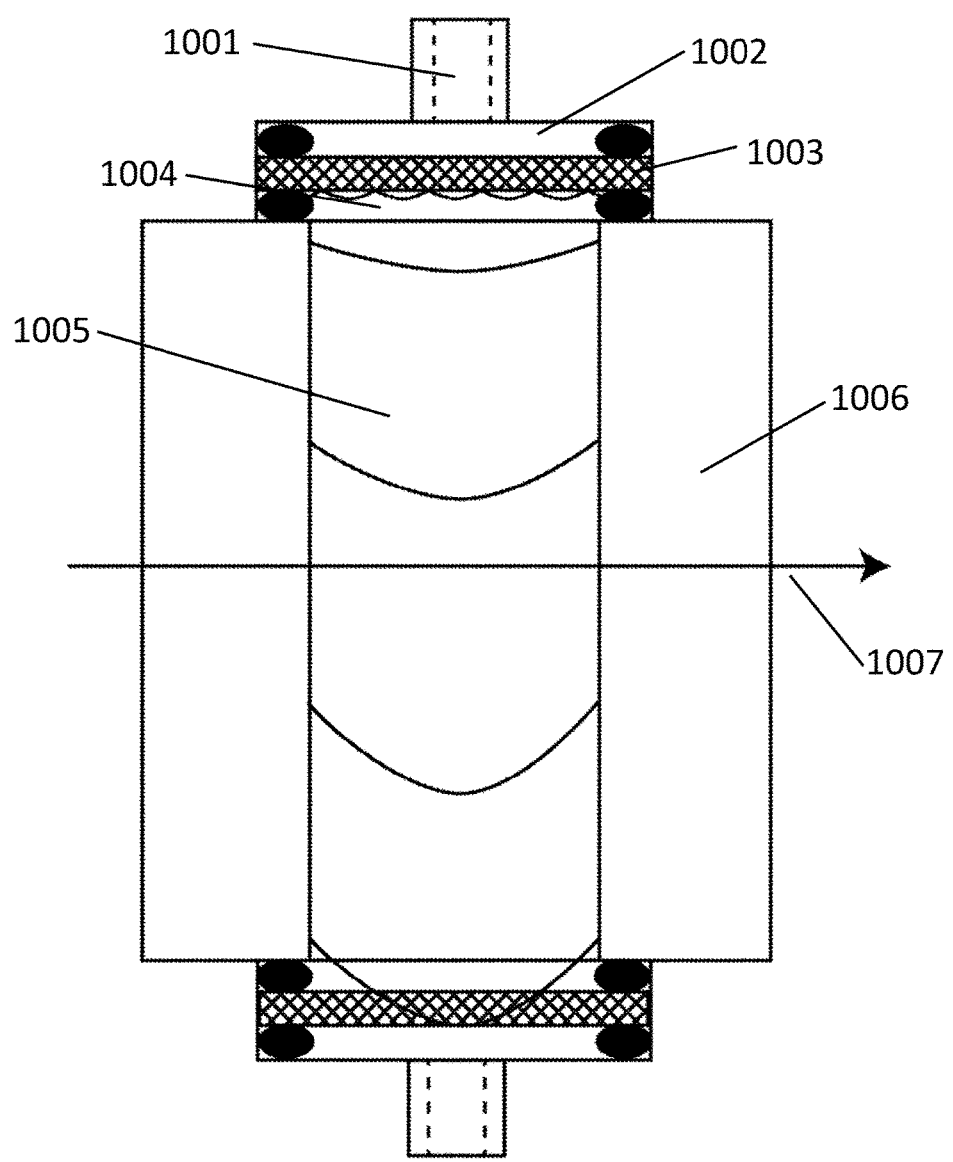
FIG. 10 illustrates an embodiment of the inventive flow system with a graphical representation of the flow profile concentration contours of a sample passing there through. Note this particular embodiment employs a flow distributor at both the inlet and the outlet of the measurement cell.

In order to promote uniform sample flow within the sample cell itself the inventive apparatus may make use of a flow distributor placed in the path of the incoming jet of fluid and/or a flow distributor placed after the outlet of the cell and prior to the outlet tubing. FIG. 10 shows a cross section of the elements of one embodiment of the present invention. The inlet tubing 1001 allows flow to enter an inlet entry volume 1002, where it thereafter passes through a porous barrier acting as the inlet flow distributor 1003. There is an impedance mismatch between the inlet tube and the detection cell which is proportional to the square of the average fluid velocity. $\Delta P_1$ defines the pressure difference required for the sample to fill the entire inlet entry volume 1002. $\Delta P_2$ defines the pressure difference required for the sample to pass from the inlet entry through the flow distributor 1003 into the cell entry volume. In order for the flow to be properly distributed transverse to the fluid flow through the cell, prior to entering the cell entry volume 1004, $\Delta P_2 \gg \Delta P_1$. The diameter of the detection cell, generally being on the order of 10 times the inner diameter of the inlet tubing, would need to generate a backpressure 10,000 times greater than the nominal back pressure of the sample cell. When this condition is achieved, one may approximate the flow velocity through the distributor 1003 as being uniform everywhere inside the volume 1002. An embodiment also including a coil at the inlet results in the sample being uniform across the orifice 1001. Given the uniform velocity through the flow distributor 1003, the sample will distribute itself to be uniform across the top surface achieving, to good approximation, plug flow.

For example, in one experimental configuration $\Delta P_1$-$\Delta P_2$ was measured at 2 psi, this is 1000 times greater than the calculated required backpressure which will only improve sample distribution as it enters the measurement cell. After passing through the flow distributor 1003, the flow enters a cell entry volume 1004 and then passes into the inner bore 1005 of the measurement cell 1006. A light beam 1007 passes through the cell and photo detectors are placed in a ring around the cell to detect scattered light. The number of photodetectors can vary from a single detector, generally located at 90° relative to the beam direction, to a plurality of detectors located at various angles.

The flow distributor itself can take many forms. In a preferred embodiment of the invention, the flow distributor is a stainless steel wire mesh with a pore size of 25 μm. Experiments by the inventors have verified that this configuration provides appreciable benefit to the uniform flow profile while minimizing the system back-pressure and the possibility of plugging. Added benefits of the use of a stainless steel mesh as a flow distributor include its compatibility with both aqueous and organic solvents, durability, and low cost. The mesh at the inlet translates a single orifice 1001 injecting sample into the cell into plurality of orifices, each of which introduces a portion of the sample into the cell. The resulting flow entering the cell resembles a plurality of Poiseuille distributions at each tiny orifice, which, when averaged together approximate plug flow as it enters flow cell. The plug flow then heals back into a large-scale Poiseuille profile as the sample traverses the measurement volume. A disc shaped frit may also act as a flow distributor.

Figure 11:
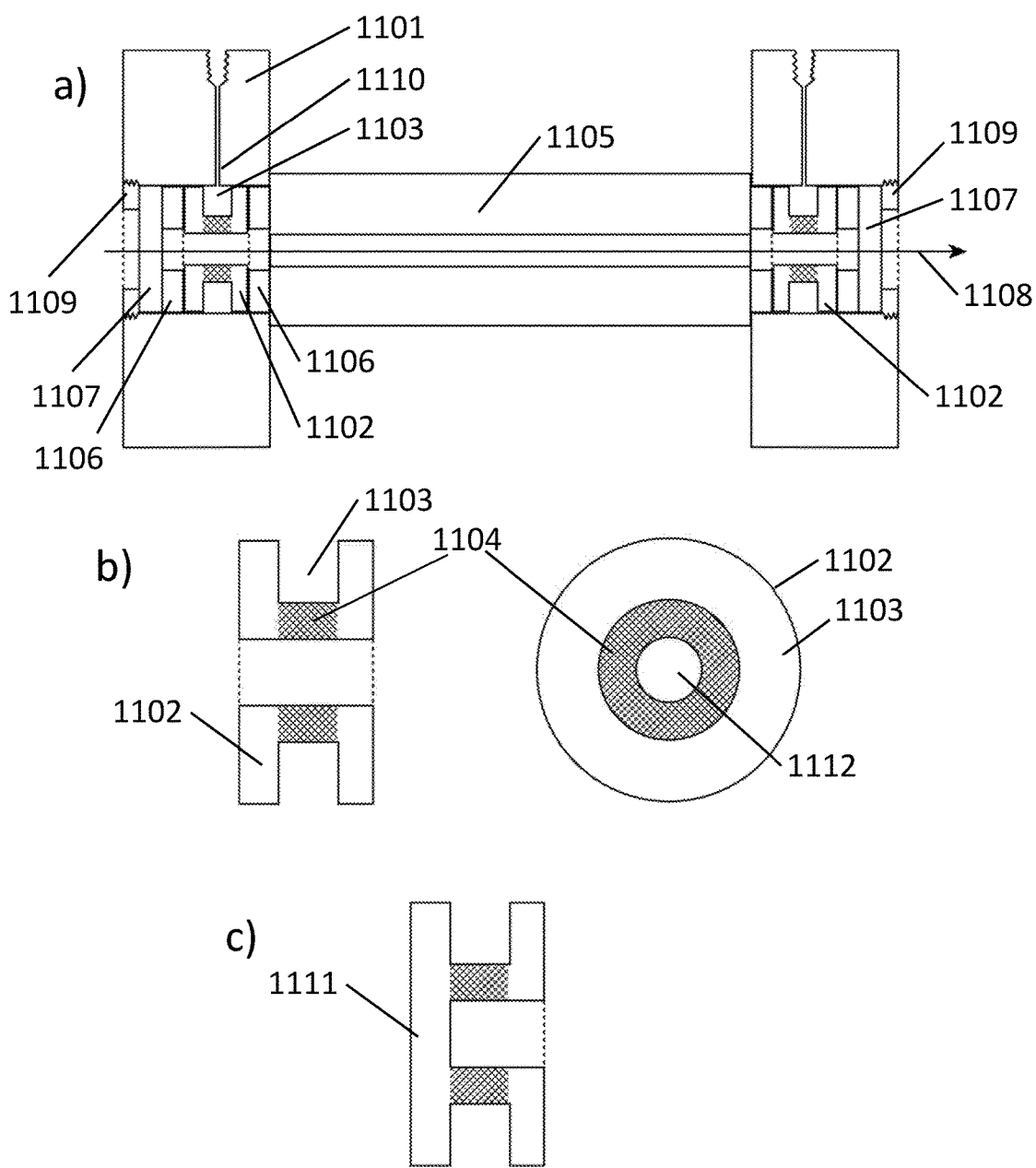
FIG. 11 shows a flow cell assembly employing an annular flow distributor in a parallel cell configuration.

In another embodiment of the invention, a spool shaped annular flow distributor can be used. This is particularly useful for light scattering measurements utilizing the parallel flow cell configuration; as a screen or frit will block the light beam passing along the measurement bore in many configurations. An example of an embodiment of a parallel cell MALS assembly in which the annular flow distributor is used is shown in FIG. 11(a), and a side and top view of the annular distributor itself is shown in FIG. 11(b). In this configuration, the sample enters a retaining inlet manifold 1101, and flow is directed into the annular distributor 1102, by means of a channel 1103 extending around the circumference of the distributor. The distributor's inner surface 1104 is porous, and tiny jets of fluid then enter the bore of the flow cell radially therefrom by first filling the empty region 1112 of the distributor. The porous element 1104 can be made of a annular frit or screen, or could be constructed as a solid annular block with a series of radial holes drilled or etched in it. The annular distributor is contained by sealing means 1106 such as gaskets or o-rings both between the cell structure 1105 and window 1107 through which the beam 1108 passes and which is held into the manifold by a retaining ring 1109. As the pressure required to fill the annular channel $\Delta P_2$ is small compared to the pressure required to pass through the porous elements of the distributor $\Delta P_1$, the condition $\Delta P_2 \ll \Delta P_1$ is satisfied and following the argument above, the sample passing thereinto is well mixed prior to entering the cell itself. The annular distributor is ideal for use with a parallel cell configuration. One could combine the annual flow distributor with flat distributor similar to described above. For example, a frit element could be placed at a position near the junction of the inlet tubing with the inlet manifold 1110 to further homogenize the sample prior to entry into the region 1103. Alternatively the annular flow distributor could be used with a cell in the perpendicular configuration, and without the need for the sealing window to be transparent, indeed, in this case there is no need for a window at all, and the annular distributor can comprise a solid end 1111, as shown in FIG. 11c, permitting thereby, fluid flow only in one direction, namely into the cell. Additionally, the annular distributor could be positioned at the outlet of the sample cell with or without a flow distributor at the inlet.

Figure 12:
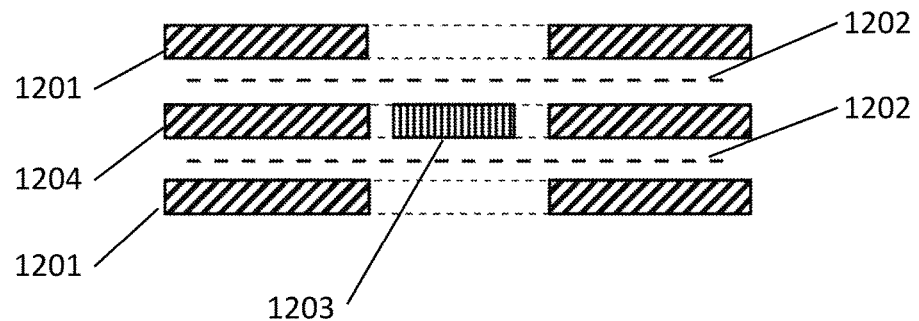
FIG. 12 illustrates a preferred embodiment of a flow distributor for the inventive measurement system wherein a square shaped flow interrupter is seated within a circular gasket sandwiched between two meshed sheets that are in turn sandwiched between another pair of circular gaskets.
Figure 12:
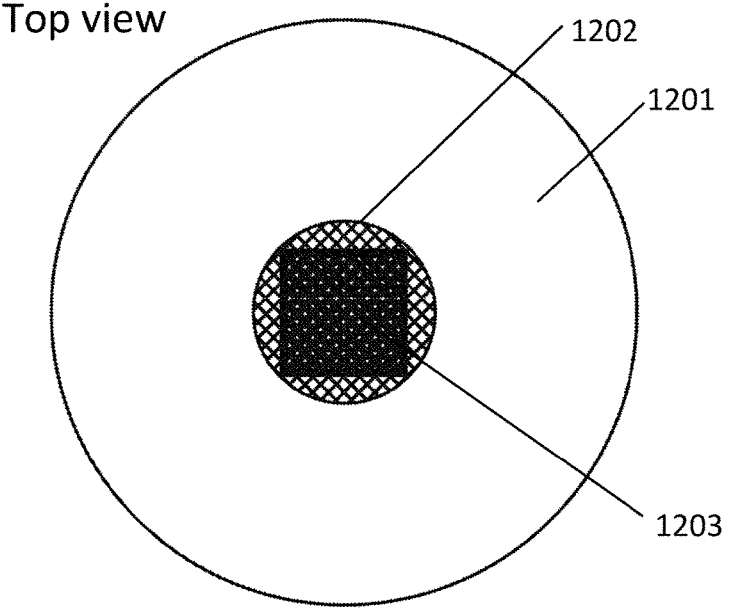

Another embodiment of the invention makes use of a novel flow disruptor placed within the flow path, either at the entrance or exit (or both) of the measurement cell. A flow disruptor may take many forms, the preferred embodiment of which is described in FIG. 12 wherein a solid blocking element 1203, made of a material which is chemically stable in the solvent to be used in the chromatography system, disrupts the incoming jet of fluid into or out of the cell. This blocking element 1203 is placed within a generally circular gasket 1204, usually made of Polytetrafluoroethylene (PTFE), the material commonly referred to by the trade name Teflon (The Chemours Company, Wilmington Del.). The blocking 1203 element may preferably be made of a shape, such as a square or an equilateral triangle, with lateral dimensions chosen such that it can be seated, without moving in a lateral direction, within the opening of the gasket 1204. The gasket 1204 and blocking element 1203 form thereby a well-defined, restricted flow path through which sample may pass from the inlet tubing to the measurement cell. The gasket and blocking element are sandwiched between two screen elements 1202 that are composed of a material which is inert in the solvent to be used in the chromatography system, such as stainless steel or nickel. The screens 1202 provide relatively uniform fluid path and are capable of retaining the sandwiched elements 1203 and 1204 in place along the flow path. The resulting sandwich is further sandwiched between two more circular PTFE gaskets 1201, which may be of identical dimensions to gasket 1204, or which may vary such that the meet spatial requirements of a manifold in which the resulting layers are contained. FIG. 12(b) shows a top view of the assembled flow distribution system.

Figure 13:
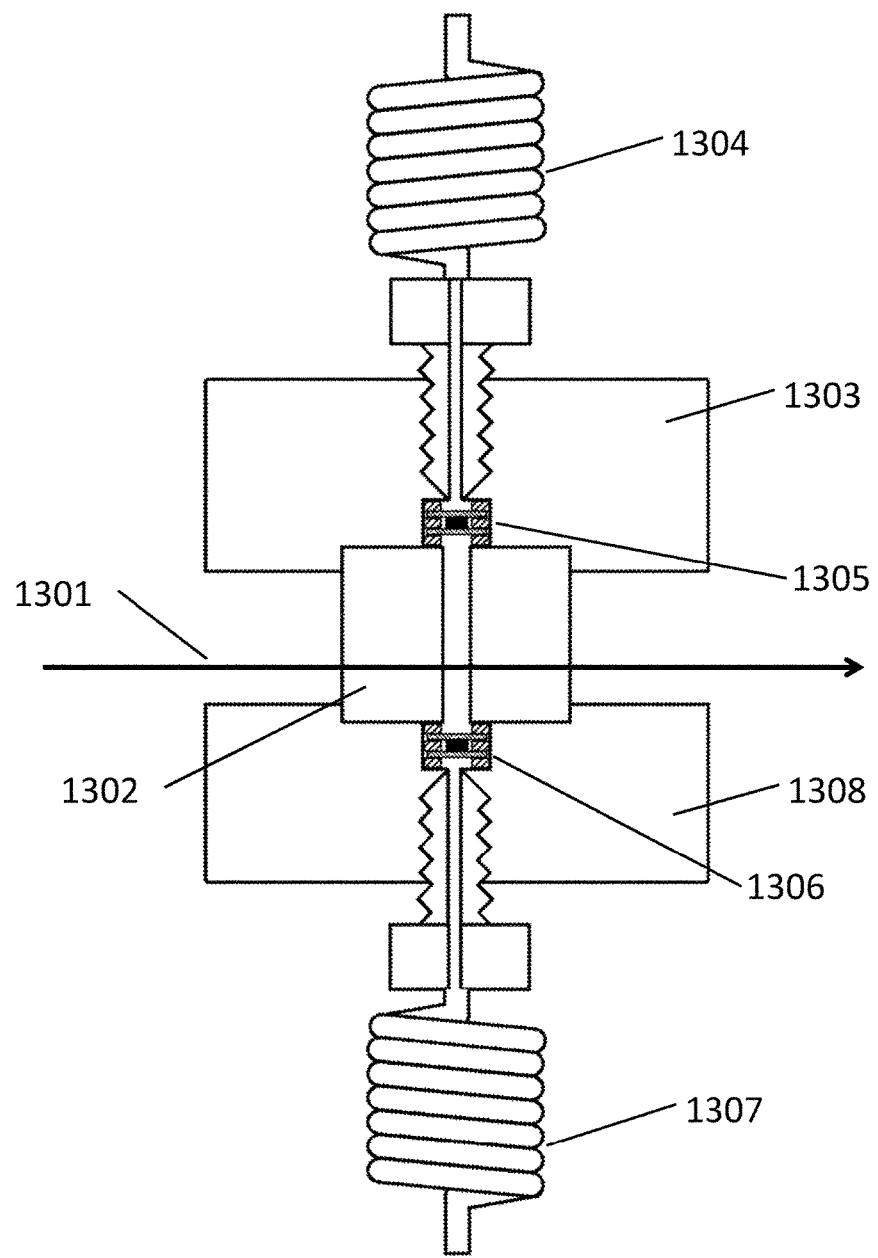
FIG. 13 shows a preferred embodiment of the invention utilizing many disclosed elements including a pair of the flow distributor sandwiches of FIG. 12 held together in the flow cell manifold that also permits the connection of coiled inlet and outlet tubes with standard fittings.

While any and all combinations of the means by which flow through a multi detector measurement cell described herein can be managed are part of the present invention, the following example sets forth a preferred embodiment combining several of the elements to optimize MALS measurements is shown in FIG. 13. In this embodiment a coiled section of tubing 1304 is connected by an inlet fitting which mounts to the top section 1303 of a manifold comprised of two halves. Sandwiched between the two manifold halves 1303 and 1308, is the optically transparent measurement cell 1302. The two halves of the manifold may be held together by bolts, clamps or other means. Flow through the inlet tubing 1304 passes through the inlet fitting and comes into contact with an inlet flow distributor 1305 which, in this embodiment is the flow disruptor shown in FIG. 12. Flow passes from the inlet flow disruptor 1305 into and through the measurement cell 1302 where it is illuminated by a fine light beam 1301 such as is generated by a laser. About the measurement cell a plurality of photodetectors are placed to measure light scattered from the illuminated beam by the sample. Upon exiting the measurement cell, the sample passes through the exit flow disruptor 1306 and into the exit tubing 1307, which is held in place within the manifold element 1308 by an outlet fitting. Inlet and outlet fittings are generally made from a material such as polyether ether ketone (PEEK) or stainless steel. Flow passing through the exit tubing 1307 may then pass on to another measurement device in the chain which may or may not contain similar fittings, coiled tubing and flow distributors or disruptors. It should be noted that the inlet and outlet tubing is shown as a short length of tightly coiled tubing 1304 and 1307 respectively in FIG. 13, however various other configurations may exist for the coiled tubing, including tubing that is tightly wound, that is loosely wound, that is extended a significant distance, that acts only Poiseuille flow disruptor (such as the small lengths shown in FIG. 13), or lengths coiled for as much of the distance between the column and the measurement cell as is reasonably possible. The same configurations are also possible and may be used between the MALS instrument and the next measurement instrument downstream from the MALS instrument. It should also be recognized that it is not necessary, though it is often preferable, that the MALS instrument be the first in line following the separation system.

While the coiled tubing is generally composed of stainless steel, this disclosure is not limited to this material alone. Other materials which can retain a coiled shape or which can be made to maintain the coiled shape while still withstanding the pressure required in an HPLC, UHPLC or other separation system, such as FFF, may also be used. For example, PEEK tubing may be coiled and held into this coiled configuration by a wire support external to the tubing. Further, while the preferred bore size for UHPLC measurements might be 100 μm, the disclosure should not be considered limited to this size, but can include any standard or custom chromatography tubing capable maintaining a coiled shape or being made to maintain a coiled shape. Possible inner sizes of this coiled tubing include 127 μm, 178 μm, 254 μm, 508 μm and 1016 μm as well as tubing of variable inner bore diameter.

Measurement of Detector Lag and Visualization of Concentration Contour Lines

The measurement lag of concentration contours between non-aligned detectors discussed above was experimentally demonstrated by injecting a standard UHPLC sample into a solvent stream and monitoring its passage through the system with a CCD camera at multiple scattering angles. Narrow strips along the breadth of the bore were monitored as the sample passed there through, and the intensity at a plurality positions was recorded. The time delay was calculated based on the arrival time of the intensity maxima recorded at each position within the measurement volume. The results of several runs can be seen in FIGS. 14-17. The presented data shows the resulting time delays, and provides a visualization of the sample front for several conditions.

Figure 14:
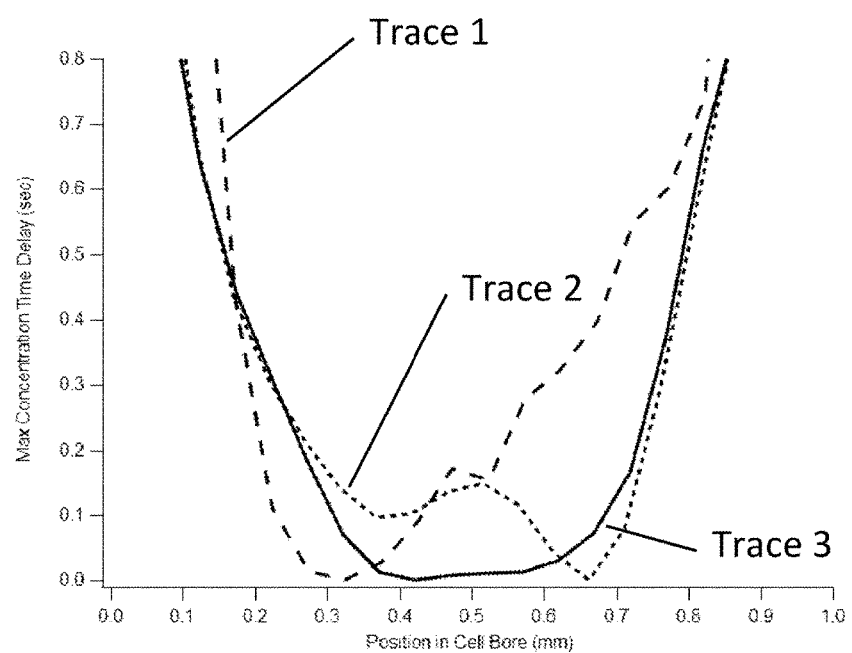
FIG. 14 presents a visualization of flow profiles in a measurement cell wherein the profiles show asymmetry due to Dean Flow caused by bent inlet tubing.

FIG. 14 graphically demonstrates the effect of Dean flow on the sample profile in the measurement cell. Trace 1 shows the flow sample profile with the inlet tubing bent slightly towards the laser beam entrance. Trace 2 shows the resultant sample profile wherein the inlet tubing is bent towards the forward monitor, opposite the laser. Trace 3 shows the profile of tubing connected to the cell in as straight a manner as possible. This data clearly indicates that small bends in the inlet tubing can create dramatically different flow profiles in the cell itself, which will cause time delay issues for slightly misaligned detectors discussed previously.

Figure 15:
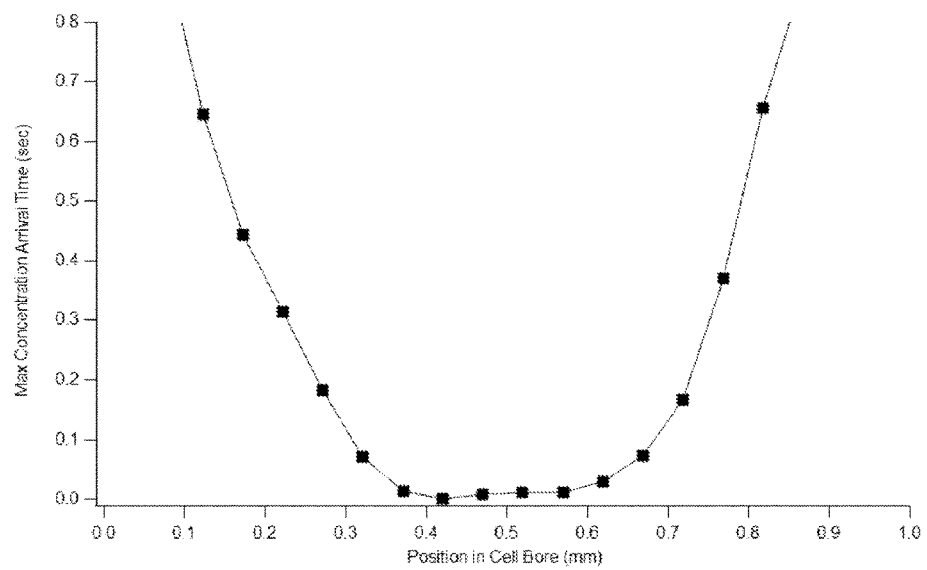
FIG. 15 illustrates the flow profile within the cell of a near ideal configuration wherein the inlet tubing is perfectly straight prior to coupling with the flow cell.

FIG. 15 illustrates a near ideal configuration wherein the inlet tubing into the flow cell is perfectly straight, and therefore has no bend radius. The flow rate used was 0.3 mL/min, the inner diameter of the inlet tubing was 100 μm and the inlet tubing length was 250 mm. A stainless steel screen was used as a flow distributor. As can be seen from the data, the contour front is relatively symmetrical, although there is still clear time dependence in the sample profile.

Figure 16:
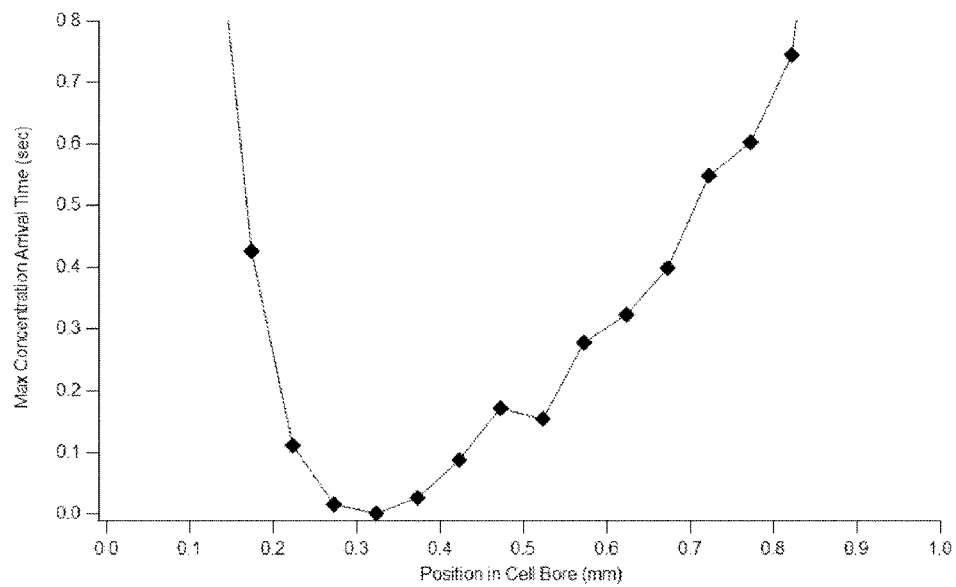
FIG. 16 illustrates asymmetry in the sample profile due to a 25 mm bend radius in the tubing prior to coupling with the flow cell.

FIG. 16, by contrast, shows severe asymmetry to the sample profile. As in the previous example, the flow rate used was 0.3 mL/min, the inner diameter of the inlet tubing was 100 μm and the inlet tubing length was 250 mm. A stainless steel screen was used as a flow distributor. However, in this example, the inlet tubing had a bend radius of 25 mm prior to entry into the cell. For this case the $Dn^2Sc$ parameter for the 25 mm bend is approximately 3500, well above the minimum value indicating tube curvature is impactful to peak dispersion.

Figure 17:
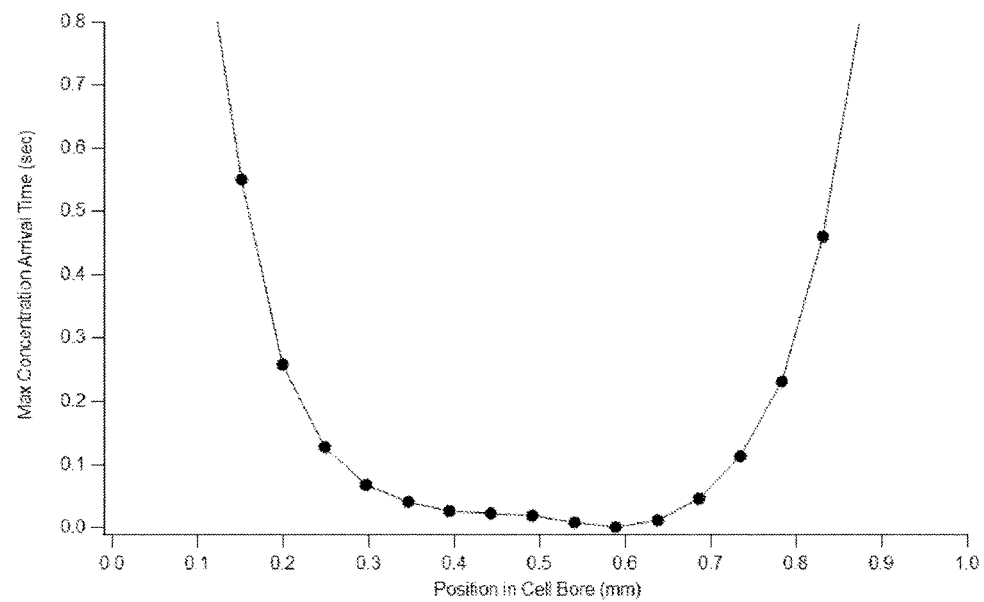
FIG. 17 illustrates the sample profile with the same bend conditions as those presented in FIG. 16, however, in this illustration, an embodiment of the invention wherein coiled inlet tubing and a mesh flow distributor are employed.

Lastly, FIG. 17 shows data collected wherein, again the tubing entering the inlet of the cell has a bend radius of about 25 mm, however a coil is added to the tubing just before entrance into the cell and after the 25 mm bend. Again, the flow rate used was 0.3 mL/min, the inner diameter of the inlet tubing was 0.004" and the inlet tubing length was 250 mm with a coil bend radius of 1.6 mm. A stainless steel screen was used as a flow distributor. As can be clearly seen, the addition of the coil with a flow distributing screen returns the profile to the symmetric state similar to that seen in FIG. 15, wherein the tubing was impractically straight. For this case the $Dn^2Sc$ parameter for the 1.6 mm coil is approximately 67000, almost 20 times the value of the 25 mm bend. The much greater $Dn^2Sc$ value of the coil compared to the inlet bend results in the dispersion created by the coil has a greater influence on the sample flow within the tube resulting in a much more uniform sample concentration, both radially and axially, before entering the sample cell.

Figure 18:
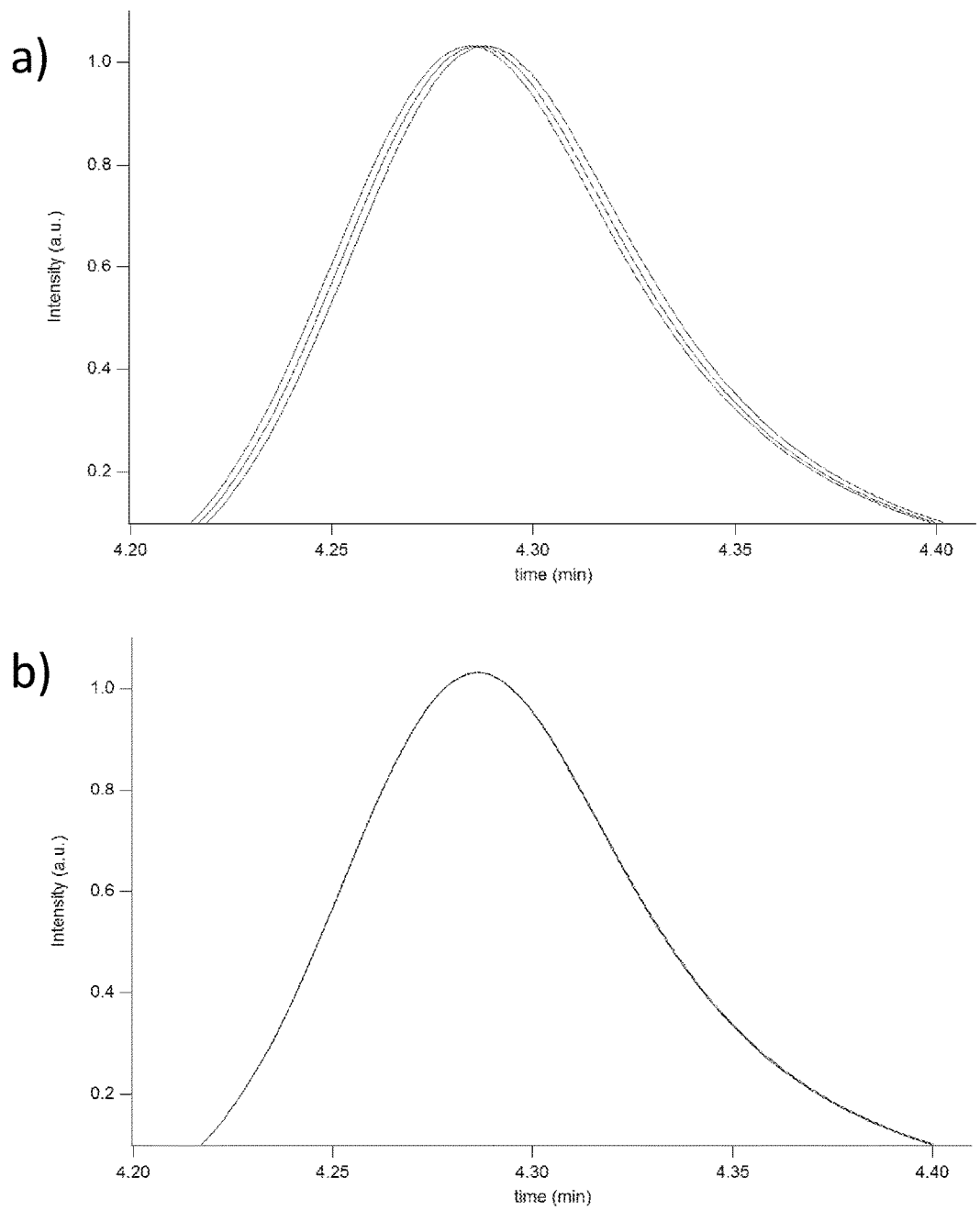
FIG. 18 contrasts two chromatograms wherein the detectors (a) are and (b) are not misaligned. Misalignment can result in significant errors.

FIG. 18 contrasts results of chromatogram traces with three detectors that are not aligned to the same sample volume within the flow cell. The detector traces have been normalized to the same amplitude to highlight that small misalignment results in a time delay between detector traces, seen in FIG. 18a. A time delay of 50 msec between the detectors could results in a radius error of up to 10%. By contrast the data shown in FIG. 18b, where each detector is seeing a similar sample volume shows all three detector signals well aligned with no appreciable delay time, resulting in an accurate measurement of the sample radius.

As will be evident to those skilled in the arts of light scattering and the characterization of macromolecules there are many obvious variations of the methods and devices of our invention that do not depart from the fundamental elements that we have listed for their practice; all such variations are but obvious implementations of the invention described hereinbefore and are included by reference to our claims, which follow.

What is claimed is:

1. An apparatus comprising:
   a coiled tube comprising a coiled tube outlet,
     wherein the coiled tube outlet is connected only to an inlet of a flow through cell configured to be viewed by detector elements,
     wherein a bend radius to bore radius ratio of the coiled tube is less than 50,
     wherein the coiled tube is configured to allow a liquid sample to flow into the inlet of the flow through cell; and
   a flow distributor housed within the inlet of the flow through cell,
     wherein the flow distributor is configured to allow the liquid sample to flow from the coiled tube, through the flow distributor, and into the flow through cell, resulting in a flow entering the flow through cell,
     wherein the flow approximates plug flow as the flow enters the flow through cell.

2. The apparatus of claim 1 wherein the flow through cell is transparent.

3. The apparatus of claim 1 wherein the coiled tube is a helix.

4. The apparatus of claim 1 wherein the flow distributor is a mesh screen.

5. The apparatus of claim 1 wherein the flow distributor is a frit.

6. The apparatus of claim 4 wherein the mesh screen is comprises stainless steel.

7. The apparatus of claim 4 wherein the mesh screen has a pore size of 25 μm.

8. The apparatus of claim 1 wherein the coiled tube comprises stainless steel.

9. The apparatus of claim 1 wherein the coiled tube has a nominal inner diameter of 127 microns.

10. A method comprising:
    flowing a particle bearing liquid sample through a coiled tube comprising a coiled tube outlet,
      wherein the coiled tube outlet is connected only to an inlet of a flow through cell configured to be viewed by detector elements, wherein a bend radius to bore radius ratio of the coiled tube is less than 50; and flowing the liquid sample from the coiled tube outlet through a flow distributor housed within the inlet of the flow through cell, resulting in a flow entering the flow through cell, wherein the flow approximates plug flow as the flow enters the flow through cell.

11. An apparatus comprising:

a coiled tube comprising a coiled tube outlet, wherein the coiled tube outlet is connected only to an inlet of a flow through cell configured to be viewed by detector elements, wherein a bend radius to bore radius ratio of the coiled tube is less than 50, wherein the coiled tube is configured to allow a liquid mixture to flow into the inlet of the flow through cell; and a flow distributor housed within the inlet of the flow through cell, wherein the flow distributor is configured to allow the liquid mixture to flow from the coiled tube, through the flow distributor, and into the flow through cell, resulting in a flow entering the flow through cell, wherein the flow approximates plug flow as the flow enters the flow through cell.

12. The apparatus of claim 11 wherein the flow distributor comprises a mesh screen.

* * * * *